United States Patent [19]
Gough et al.

[11] Patent Number: 5,928,229
[45] Date of Patent: *Jul. 27, 1999

[54] TUMOR ABLATION APPARATUS

[75] Inventors: Edward J. Gough, Menlo Park; Alan A. Stein, Moss Beach, both of Calif.

[73] Assignee: Rita Medical Systems, Inc., Mountain View, Calif.

[*] Notice: This patent is subject to a terminal disclaimer.

[21] Appl. No.: 08/961,325

[22] Filed: Oct. 30, 1997

Related U.S. Application Data

[63] Continuation-in-part of application No. 08/515,379, Aug. 15, 1995, Pat. No. 5,683,384, which is a continuation-in-part of application No. 08/290,031, Aug. 12, 1994, Pat. No. 5,536,267, which is a continuation-in-part of application No. 08/148,439, Nov. 8, 1993, Pat. No. 5,458,597.

[51] Int. Cl.⁶ ..................................................... A61B 17/39
[52] U.S. Cl. .............................. 606/41; 606/48; 606/42; 607/101; 607/102
[58] Field of Search ........................... 606/41, 42, 45–50; 607/100–102, 115, 116, 128; 604/21, 22

[56] References Cited

U.S. PATENT DOCUMENTS

| | | |
|---|---|---|
| Re. 32,057 | 12/1985 | LeVeen . |
| Re. 32,066 | 1/1986 | LeVeen . |
| Re. 34,086 | 10/1992 | George . |
| 3,474,777 | 10/1969 | Figge et al. . |
| 3,834,392 | 9/1974 | Lampman et al. . |
| 3,858,586 | 1/1975 | Lessen . |
| 3,987,795 | 10/1976 | Morrison, Jr. . |
| 3,991,770 | 11/1976 | LeVeen . |
| 4,011,872 | 3/1977 | Komiya . |
| 4,016,881 | 4/1977 | Rioux et al. . |
| 4,016,886 | 4/1977 | Doss . |
| 4,026,301 | 5/1977 | Friedman et al. . |
| 4,033,351 | 7/1977 | Hetzel . |
| 4,043,342 | 8/1977 | Morrison, Jr. . |
| 4,074,718 | 2/1978 | Morrison, Jr. . |

(List continued on next page.)

FOREIGN PATENT DOCUMENTS

| | | |
|---|---|---|
| 0 370 890 | 5/1990 | European Pat. Off. . |
| 0 462 302 | 12/1991 | European Pat. Off. . |
| 0 472 368B1 | 2/1992 | European Pat. Off. . |
| 0 502 268 | 9/1992 | European Pat. Off. . |
| 0 519 415 | 12/1992 | European Pat. Off. . |
| 0 566 450B1 | 10/1993 | European Pat. Off. . |
| 0 608 609 | 8/1994 | European Pat. Off. . |
| 2 283 701 | 4/1976 | France . |
| 2 670 664 | 6/1992 | France . |
| 10 07 960 | 10/1957 | Germany . |
| 21 24 684 | 11/1973 | Germany . |
| 89 09 492 U | 3/1990 | Germany . |
| 38 38 840 | 5/1990 | Germany . |
| 39 30 451 | 3/1991 | Germany . |
| 41 00 422 | 7/1992 | Germany . |
| 63-275632 | 11/1988 | Japan . |
| 2-121675 | 5/1990 | Japan . |
| WO 92/10142 | 6/1992 | WIPO . |
| WO 94/04220 | 3/1994 | WIPO . |
| WO 94/10925 | 5/1994 | WIPO . |
| WO 94/11059 | 5/1994 | WIPO . |
| WO 94/17856 | 8/1994 | WIPO . |
| WO 94/25110 | 11/1994 | WIPO . |
| WO 94/26178 | 11/1994 | WIPO . |
| WO 95/19142 | 7/1995 | WIPO . |
| WO 95/25471 | 9/1995 | WIPO . |
| WO 96/04860 | 2/1996 | WIPO . |
| WO 96/29946 | 10/1996 | WIPO . |
| WO 97/06739 | 2/1997 | WIPO . |

*Primary Examiner*—Michael Peffley
*Attorney, Agent, or Firm*—Wilson Sonsini Goodrich & Rosati

[57] ABSTRACT

An ablation apparatus has a multiple antenna device with a primary antenna and a secondary antenna positionable in a lumen of the primary antenna. The secondary antenna is at least partially deployable from the primary antenna in a lateral direction relative to a longitudinal axis of the primary antenna with at least one radius of curvature. A distal end of the primary antenna is sufficiently sharp to pierce tissue. The primary and secondary antennas are configured to provide a selectable geometric ablation of a selected tissue mass. An insulation sleeve is positioned on an exterior of the primary antenna. One or more cables are coupled to the multiple antenna device.

25 Claims, 8 Drawing Sheets

U.S. PATENT DOCUMENTS

| | | |
|---|---|---|
| 4,080,959 | 3/1978 | LeVeen . |
| 4,085,756 | 4/1978 | Weaver . |
| 4,095,602 | 6/1978 | LeVeen . |
| 4,119,102 | 10/1978 | LeVeen . |
| 4,121,592 | 10/1978 | Whalley . |
| 4,140,130 | 2/1979 | Storm, III . |
| 4,154,246 | 5/1979 | LeVeen . |
| 4,230,129 | 10/1980 | LeVeen . |
| 4,237,898 | 12/1980 | Whalley . |
| 4,269,174 | 5/1981 | Adair . |
| 4,285,346 | 8/1981 | Armitage . |
| 4,289,135 | 9/1981 | Nordensrom et al. . |
| 4,290,435 | 9/1981 | Waggott . |
| 4,303,636 | 12/1981 | Gordon . |
| 4,331,654 | 5/1982 | Morris . |
| 4,337,760 | 7/1982 | Rubin . |
| 4,345,588 | 8/1982 | Widder et al. . |
| 4,346,715 | 8/1982 | Gammell . |
| 4,375,220 | 3/1983 | Matvias . |
| 4,409,993 | 10/1983 | Furihata . |
| 4,411,266 | 10/1983 | Cosman . |
| 4,418,692 | 12/1983 | Guay . |
| 4,461,283 | 7/1984 | Doi . |
| 4,506,680 | 3/1985 | Stokes . |
| 4,512,762 | 4/1985 | Spears . |
| 4,524,770 | 6/1985 | Orandi . |
| 4,532,924 | 8/1985 | Auth et al. . |
| 4,545,368 | 10/1985 | Rand et al. . |
| 4,562,838 | 1/1986 | Walker . |
| 4,565,200 | 1/1986 | Cosman . |
| 4,574,782 | 3/1986 | Borrelli et al. . |
| 4,583,556 | 4/1986 | Hines et al. . |
| 4,586,490 | 5/1986 | Katz . |
| 4,601,296 | 7/1986 | Yerushalmi . |
| 4,648,892 | 3/1987 | Kittrell et al. . |
| 4,652,257 | 3/1987 | Chang . |
| 4,658,819 | 4/1987 | Harris et al. . |
| 4,660,571 | 4/1987 | Hess et al. . |
| 4,662,359 | 5/1987 | Gordon . |
| 4,676,258 | 6/1987 | Inokuchi et al. . |
| 4,690,130 | 9/1987 | Mirell . |
| 4,692,139 | 9/1987 | Stiles . |
| 4,709,701 | 12/1987 | Weber . |
| 4,753,248 | 6/1988 | Engler et al. . |
| 4,763,671 | 8/1988 | Goffinet . |
| 4,776,086 | 10/1988 | Kasevich et al. . |
| 4,800,899 | 1/1989 | Elliott . |
| 4,813,429 | 3/1989 | Eshel et al. . |
| 4,818,542 | 4/1989 | DeLuca et al. . |
| 4,823,791 | 4/1989 | D'Amelio et al. . |
| 4,823,793 | 4/1989 | Angulo et al. . |
| 4,825,880 | 5/1989 | Stauffer et al. . |
| 4,838,265 | 6/1989 | Cosman et al. . |
| 4,846,196 | 7/1989 | Wiksell et al. . |
| 4,860,744 | 8/1989 | Johnson et al. . |
| 4,862,887 | 9/1989 | Weber et al. . |
| 4,881,543 | 11/1989 | Trembly et al. . |
| 4,887,614 | 12/1989 | Shirakami et al. . |
| 4,907,589 | 3/1990 | Cosman . |
| 4,920,978 | 5/1990 | Colvin . |
| 4,931,047 | 6/1990 | Broadwin et al. . |
| 4,940,064 | 7/1990 | DeSai . |
| 4,945,912 | 8/1990 | Langberg . |
| 4,947,842 | 8/1990 | Marchosky et al. . |
| 4,950,267 | 8/1990 | Ishihara et al. . |
| 4,962,761 | 10/1990 | Golden . |
| 4,963,364 | 10/1990 | Fox et al. . |
| 4,966,604 | 10/1990 | Reiss . |
| 4,976,680 | 12/1990 | Hayman et al. . |
| 4,976,711 | 12/1990 | Parins et al. . |
| 4,983,159 | 1/1991 | Rand . |
| 4,985,022 | 1/1991 | Fearnot et al. . |
| 4,989,601 | 2/1991 | Marchosky et al. . |
| 5,003,991 | 4/1991 | Takayama et al. . |
| 5,007,908 | 4/1991 | Rydell . |
| 5,009,656 | 4/1991 | Reimels . |
| 5,010,897 | 4/1991 | LeVeen . |
| 5,011,483 | 4/1991 | Sleister . |
| 5,013,312 | 5/1991 | Parins et al. . |
| 5,015,227 | 5/1991 | Broadwin et al. . |
| 5,016,615 | 5/1991 | Driller et al. . |
| 5,026,959 | 6/1991 | Ito et al. . |
| 5,047,027 | 9/1991 | Rydell . |
| 5,055,100 | 10/1991 | Olsen . |
| 5,057,107 | 10/1991 | Parins et al. . |
| 5,059,199 | 10/1991 | Okada et al. . |
| 5,067,952 | 11/1991 | Gudov et al. . |
| 5,071,419 | 12/1991 | Rydell et al. . |
| 5,078,717 | 1/1992 | Parins et al. . |
| 5,080,660 | 1/1992 | Buelna . |
| 5,083,565 | 1/1992 | Parins . |
| 5,084,001 | 1/1992 | Van't Hooft et al. . |
| 5,084,045 | 1/1992 | Helenowski . |
| 5,085,659 | 2/1992 | Rydell . |
| 5,099,756 | 3/1992 | Franconi et al. . |
| 5,100,423 | 3/1992 | Fearnot . |
| 5,115,818 | 5/1992 | Holleman et al. . |
| 5,119,832 | 6/1992 | Xavier . |
| 5,122,137 | 6/1992 | Lennox . |
| 5,125,928 | 6/1992 | Parins et al. . |
| 5,128,147 | 7/1992 | LeVeen et al. . |
| 5,156,151 | 10/1992 | Imran . |
| 5,167,626 | 12/1992 | Casper et al. . |
| 5,169,396 | 12/1992 | Dowlatshahi et al. . |
| 5,170,789 | 12/1992 | Narayan et al. . |
| 5,170,805 | 12/1992 | Kensey et al. . |
| 5,178,620 | 1/1993 | Eggers et al. . |
| 5,183,455 | 2/1993 | Hayman et al. . |
| 5,190,517 | 3/1993 | Zieve et al. . |
| 5,190,539 | 3/1993 | Fletcher et al. . |
| 5,190,541 | 3/1993 | Abele . |
| 5,190,766 | 3/1993 | Ishihara . |
| 5,197,466 | 3/1993 | Marchosky et al. . |
| 5,197,963 | 3/1993 | Parins . |
| 5,197,964 | 3/1993 | Parins . |
| 5,203,353 | 4/1993 | Easley et al. . |
| 5,203,782 | 4/1993 | Gudov et al. . |
| 5,205,289 | 4/1993 | Hardy et al. . |
| 5,207,675 | 5/1993 | Canady . |
| 5,215,103 | 6/1993 | DeSai . |
| 5,217,458 | 6/1993 | Parins . |
| 5,222,953 | 6/1993 | Dowlatshahi . |
| 5,236,410 | 8/1993 | Granov et al. . |
| 5,236,424 | 8/1993 | Imran . |
| 5,246,438 | 9/1993 | Langberg . |
| 5,249,585 | 10/1993 | Turner et al. . |
| 5,251,645 | 10/1993 | Fenn . |
| 5,252,922 | 10/1993 | Larson, III . |
| 5,257,451 | 11/1993 | Edwards et al. . |
| 5,258,006 | 11/1993 | Rydell et al. . |
| 5,259,394 | 11/1993 | Bens . |
| 5,259,395 | 11/1993 | Li . |
| 5,267,994 | 12/1993 | Gentelia et al. . |
| 5,273,535 | 12/1993 | Edwards et al. . |
| 5,275,162 | 1/1994 | Edwards et al. . |
| 5,277,696 | 1/1994 | Hagen . |
| 5,281,213 | 1/1994 | Milder et al. . |
| 5,281,217 | 1/1994 | Edwards et al. . |
| 5,281,218 | 1/1994 | Imran . |
| 5,282,797 | 2/1994 | Chess . |
| 5,286,253 | 2/1994 | Fucci . |
| 5,290,286 | 3/1994 | Parins . |

| | | | | | | |
|---|---|---|---|---|---|---|
| 5,293,869 | 3/1994 | Edwards et al. | | 5,456,682 | 10/1995 | Edwards et al. |
| 5,295,955 | 3/1994 | Rosen et al. | | 5,458,596 | 10/1995 | Lax et al. |
| 5,300,068 | 4/1994 | Rosar et al. | | 5,458,597 | 10/1995 | Edwards et al. |
| 5,300,069 | 4/1994 | Hunsberger et al. | | 5,462,521 | 10/1995 | Brucker et al. |
| 5,300,099 | 4/1994 | Rudie . | | 5,470,308 | 11/1995 | Edwards et al. |
| 5,304,214 | 4/1994 | DeFord et al. | | 5,470,309 | 11/1995 | Edwards et al. |
| 5,309,910 | 5/1994 | Edwards et al. | | 5,471,982 | 12/1995 | Edwards et al. |
| 5,313,943 | 5/1994 | Houser et al. | | 5,472,441 | 12/1995 | Edwards et al. |
| 5,314,466 | 5/1994 | Stern et al. | | 5,484,400 | 1/1996 | Edwards et al. |
| 5,322,503 | 6/1994 | DeSai . | | 5,486,161 | 1/1996 | Lax et al. |
| 5,328,467 | 7/1994 | Edwards et al. | | 5,500,012 | 3/1996 | Brucker et al. |
| 5,334,193 | 8/1994 | Nardella . | | 5,505,730 | 4/1996 | Edwards . |
| 5,334,206 | 8/1994 | Daikuzono . | | 5,507,743 | 4/1996 | Edwards et al. |
| 5,336,222 | 8/1994 | Durgin, Jr. et al. | | 5,509,419 | 4/1996 | Edwards et al. |
| 5,342,357 | 8/1994 | Nardella . | | 5,514,130 | 5/1996 | Baker . |
| 5,348,554 | 9/1994 | Imran et al. | | 5,514,131 | 5/1996 | Edwards . |
| 5,354,296 | 10/1994 | Turkel . | | 5,520,684 | 5/1996 | Imran . |
| 5,363,861 | 11/1994 | Edwards et al. | | 5,531,676 | 7/1996 | Edwards et al. |
| 5,365,926 | 11/1994 | DeSai . | | 5,531,677 | 7/1996 | Lundquist et al. |
| 5,366,490 | 11/1994 | Edwards et al. | | 5,536,240 | 7/1996 | Edwards et al. |
| 5,368,592 | 11/1994 | Stern et al. | | 5,536,267 | 7/1996 | Edwards et al. |
| 5,370,675 | 12/1994 | Edwards et al. | | 5,540,655 | 7/1996 | Edwards et al. |
| 5,370,678 | 12/1994 | Edwards et al. | | 5,542,915 | 8/1996 | Edwards et al. |
| 5,383,876 | 1/1995 | Nardella . | | 5,542,916 | 8/1996 | Hirsch et al. |
| 5,383,917 | 1/1995 | DeSai et al. | | 5,542,928 | 8/1996 | Evans et al. |
| 5,385,544 | 1/1995 | Edwards et al. | | 5,545,161 | 8/1996 | Imran . |
| 5,397,339 | 3/1995 | DeSai . | | 5,545,171 | 8/1996 | Sharkey et al. |
| 5,398,683 | 3/1995 | Edwards et al. | | 5,545,193 | 8/1996 | Fleischman et al. |
| 5,401,272 | 3/1995 | Perkins . | | 5,546,267 | 8/1996 | Frederiksen et al. |
| 5,403,311 | 4/1995 | Abele et al. | | 5,548,597 | 8/1996 | Edwards et al. |
| 5,405,346 | 4/1995 | Grundy et al. | | 5,549,108 | 8/1996 | Edwards et al. |
| 5,409,453 | 4/1995 | Lundquist et al. | | 5,549,644 | 8/1996 | Lundquist et al. |
| 5,411,025 | 5/1995 | Webster, Jr. | | 5,554,110 | 9/1996 | Edwards et al. |
| 5,417,687 | 5/1995 | Nardella . | | 5,556,377 | 9/1996 | Rosen et al. |
| 5,421,819 | 6/1995 | Edwards et al. | | 5,558,672 | 9/1996 | Edwards et al. |
| 5,423,807 | 6/1995 | Milder . | | 5,558,673 | 9/1996 | Edwards et al. |
| 5,423,808 | 6/1995 | Edwards et al. | | 5,560,358 | 10/1996 | Arnold et al. |
| 5,423,811 | 6/1995 | Imran et al. | | 5,562,703 | 10/1996 | DeSai . |
| 5,433,708 | 7/1995 | Nichols et al. | | 5,599,345 | 2/1997 | Edwards et al. |
| 5,435,805 | 7/1995 | Edwards et al. | | 5,599,346 | 2/1997 | Edwards et al. |
| 5,437,662 | 8/1995 | Nardella . | | 5,609,151 | 3/1997 | Mulier et al. |
| 5,437,664 | 8/1995 | Cohen et al. | | 5,620,481 | 4/1997 | DeSai et al. |
| 5,456,662 | 10/1995 | Edwards et al. | | 5,855,576 | 1/1999 | LeVeen et al. .......................... 606/41 |

TUMOR ABLATION APPARATUS

REFERENCE TO RELATED APPLICATION

This application is a continuation-in-part of U.S. Pat. application Ser. No. 08/515,379, filed Aug. 15, 1995, by Edward Gough, et al., now U.S. Pat. No. 5,683,384 which is a continuation-in-part of U.S. application No. 08/290,081, filed Aug. 12, 1994, now U.S. Pat. No. 5,536,267, issued Jul. 16, 1996, by Stuart D. Edwards et al, which is a continuation-in-part of U.S. Pat. application Ser. No. 08/148,439, filed Nov. 8, 1993, entitled "Device for Treating Cancer and Non-Malignant Tumors and Methods", by Stuart D. Edwards et al., now U.S. Pat. No. 5,458,597 all of which are herein incorporated by reference.

BACKGROUND OF THE INVENTION

1. Field of the Invention

This invention relates generally to an apparatus for the treatment and ablation of body masses, such as tumors, and more particularly, to an RF treatment apparatus suitable for multi-modality treatment that includes a primary antenna is inserted into or adjacent to the tumor, and one or more side deployed secondary antennas that are less rigid than the primary antenna.

2. Description of the Related Art

Current open procedures for treatment of tumors are extremely disruptive and cause a great deal of damage to healthy tissue. During the surgical procedure, the physician must exercise care in not cutting the tumor in a manor that creates seeding of the tumor, resulting in metastasis. In recent years, development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective cancer cell eradication by hyperthermia are not completely understood. However, four cellular effects of hyperthermia on cancerous tissue have been proposed, (i) changes in cell or nuclear membrane permeability or fluidity, (ii) cytoplasmic lysomal disintegration, causing release of digestive enzymes, (iii) protein thermal damage affecting cell respiration and the synthesis of DNA or RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the skin. Certain techniques have been developed with microwave radiation and ultrasound to focus energy at various desired depths. RF applications may be used at depth during surgery. However, the extent of localization is generally poor, with the result that healthy tissue may be harmed. Induction heating gives rise to poor localization of the incident energy as well. Although induction heating may be achieved by placing an antenna on the surface of the body, superficial eddy currents are generated in the immediate vicinity of the antenna, when it is driven using RF current, and unwanted surface heating occurs with little heat delivered to the underlying tissue.

Thus, non-invasive procedures for providing heat to internal tumors have had difficulties in achieving substantial specific and selective treatment.

Hyperthermia, which can be produced from an RF or microwave source, applies heat to tissue, but does not exceed 45 degrees C., so that normal cells survive. In thermotherapy, heat energy of greater than 45 degrees C. is applied resulting in histological damage, desiccation and the denaturization of proteins. Hyperthermia has been applied more recently for therapy of malignant tumors. In hyperthermia, it is desirable to induce a state of hyperthermia that is localized by interstitial current heating to a specific area while concurrently insuring minimum thermal damage to healthy surrounding tissue. Often, the tumor is located subcutaneously and addressing the tumor requires either surgery, endoscopic procedures or external radiation. It is difficult to externally induce hyperthermia in deep body tissue because current density is diluted due to its absorption by healthy tissue. Additionally, a portion of the RF energy is reflected at the muscle/fat and bone interfaces which adds to the problem of depositing a known quantity of energy directly on a small tumor.

Attempts to use interstitial local hyperthermia have not proven to be very successful. Results have often produced nonuniform temperatures throughout the tumor. It is believed that tumor mass reduction by hyperthermia is related to thermal dose. Thermal dose is the minimum effective temperature applied throughout the tumor mass for a defined period of time. Because blood flow is the major mechanism of heat loss for tumors being heated, and blood flow varies throughout the tumor, more even heating of tumor tissue is needed to ensure effective treatment.

The same is true for ablation of the tumor itself through the use of RF energy. Different methods have been utilized for the RF ablation of masses such as tumors. Instead of heating the tumor it is ablated through the application of energy. This process has been difficult to achieve due to a variety of factors including, (i) positioning of the RF ablation electrodes to effectively ablate all of the mass, (ii) introduction of the RF ablation electrodes to the tumor site and (iii) controlled delivery and monitoring of RF energy to achieve successful ablation without damage to non-tumor tissue.

There have been a number of different treatment methods and devices for minimally invasively treating tumors. One such example is an endoscope that produces PF hyperthermia in tumors, as disclosed in U.S. Pat. No. 4,920,978. A microwave endoscope device is described in U.S. Pat. No. 4,409,993. In U.S. Pat. No. 4,920,978, an endoscope for RF hyperthermia is disclosed.

In U.S. Pat. No. 4,763,671 (the "'671 patent"), a minimally invasive procedure utilizes two catheters that are inserted interstitially into the tumor. The catheter includes a hard plastic support member. Around the support member is a conductor in the form of an open mesh. A layer of insulation is secured to the conductor with adhesive beads. It covers all of the conductor except a preselected length which is not adjustable. Different size tumors cannot be treated with the same electrode. A tubular sleeve is introduced into the support member and houses radioactive seeds. The device of the '671 patent fails to provide for the introduction of a fluidics medium, such as a chemotherapeutic agent, to the tumor for improved treatment. The size of the electrode conductive surface is not variable. Additionally, the device of the '671 patent is not capable of maintaining a preselected level of power that is independent of changes in voltage or current.

In U.S. Pat. No. 4,565,200 (the "'200 patent"), an electrode system is described in which a single entrance tract cannula is used to introduce an electrode into a selected body site. The device of the '200 patent is limited in that the single entrance tract fails to provide for the introduction, and removal of a variety of inserts, including but not limited to an introducer, fluid infusion device and insulation sleeve. Additionally, the device of the '200 patent fails to provide for the maintenance of a selected power independent of changes in current or voltage.

There is a need for an ablation device that has two or more antennas, with the first being initially introduced into or adjacent to a tumor or other solid mass, and the second antenna then laterally deployed into the tumor or solid mass, and the first antenna has a greater rigidity than the second antenna. There is a further need for an ablation device which defines a therapy zone based on a primary antenna with secondary antennas extending from the primary electrode to define the border or periphery of the ablation zone. There is still a further need for an ablation apparatus which includes a primary antenna and secondary antennas that uses temperature and/or impedance with feedback control to define the border or periphery of the ablation zone.

SUMMARY OF THE INVENTION

Accordingly, it is an object of the invention to provide an ablation apparatus with a primary antenna that is introduced into a selected solid mass and secondary antennas that are deployed laterally from the primary antenna to define a border of the ablation volume which can be of a variable geometry.

Another object of the present invention is to provide an RF treatment apparatus with a multiple antenna device that is introduced into a selected mass, and each if the antennas has a selectable length to ablate a desired geometry of the selected mass.

A further object of the invention is to provide a microwave treatment apparatus with a multiple antenna that is introduced into a selected mass, and each if the antennas has a selectable length to ablate a desired geometry of the selected mass.

Yet another object of the invention is to provide an ablation apparatus that is introduced into a selected mass, defines the periphery of a selected ablation volume during the ablation process, and achieves the ablation with RF energy, microwave energy, laser energy, or any combination thereof.

Another object of the invention is to provide a multiple antenna ablation apparatus which has a primary antenna that is constructed to be more structurally rigid than a secondary antenna, and the primary and secondary antennas are multiplexed.

A further object of the invention is to provide a multiple antenna ablation apparatus which has a primary antenna, one or more secondary antennas, and the apparatus is capable of movement in two or more planes to create a selectable ablation volume extending generally from the primary antenna to the secondary antennas.

Yet a further object of the invention is to provide a multiple antenna ablation apparatus with adjustable length antennas.

Another object of the invention is to provide a multiple antenna ablation apparatus with adjustable length insulation sleeves position on an exterior of one or both of a primary antenna and a secondary antenna.

A further object of the invention is to provide a multiple antenna ablation apparatus that includes an ability to introduce a variety of infusion mediums.

Another object of the invention is to provide an ablation apparatus including multiple antennas, sensors to detect impedance or temperature, and a sensor feedback apparatus to maintain a tissue adjacent to one of the primary or secondary antennas at a desired temperature.

These and other objectives are achieved in an ablation apparatus with a multiple antenna device. The multiple antenna device includes a primary antenna with a longitudinal axis, and a secondary antenna positionable in a lumen of the primary antenna. The secondary antenna is at least partially deployable from the primary antenna in a lateral direction relative to the longitudinal axis with at least one radius of curvature. A distal end of the primary antenna is sufficiently sharp to pierce tissue. The primary and secondary antennas are configured to provide a selectable geometric ablation of a selected tissue mass. An insulation sleeve is positioned on an exterior of the primary antenna. One or more cables are coupled to the multiple antenna device.

The multiple antenna device can be an RF antenna, an optical fiber for coherent or incoherent light, a microwave antenna, a short wave antenna and the like. At least two secondary antennas can be included with each one being capable of being laterally deployed along different points along the longitudinal axis. The secondary antenna is retractable into the primary antenna, permitting repositioning of the primary antenna. When the multiple antenna is an RF antenna, it can be operated in mono-polar or bipolar modes, and is capable of switching between the two.

Further, the multiple antenna device can be a multi-modality apparatus. One or all of the antennas can be hollow to receive an infusion medium from an infusion source and introduce the infusion medium into a selected tissue mass. A multiplexer can be coupled to the primary antenna, secondary antenna and power supply to effect multiplexing between the primary and secondary antennas.

One or more sensors are positioned at an interior or exterior of the primary or secondary antennas to detect impedance or temperature. Resources are connected with the sensors, antennas and the energy source. The resources provide an output for delivering and maintaining a selected energy at the antennas.

When the ablation apparatus includes a multiple arm device of adjustable length, at least one of the arms is hollow and adapted to receive a laser optical fiber. The other arms can be capable of delivering RF, microwave or short wave energy. Additionally, one or more of the arms is capable of delivering an infusion medium, providing multi-modality treatment.

DETAILED DESCRIPTION

Figure 1:
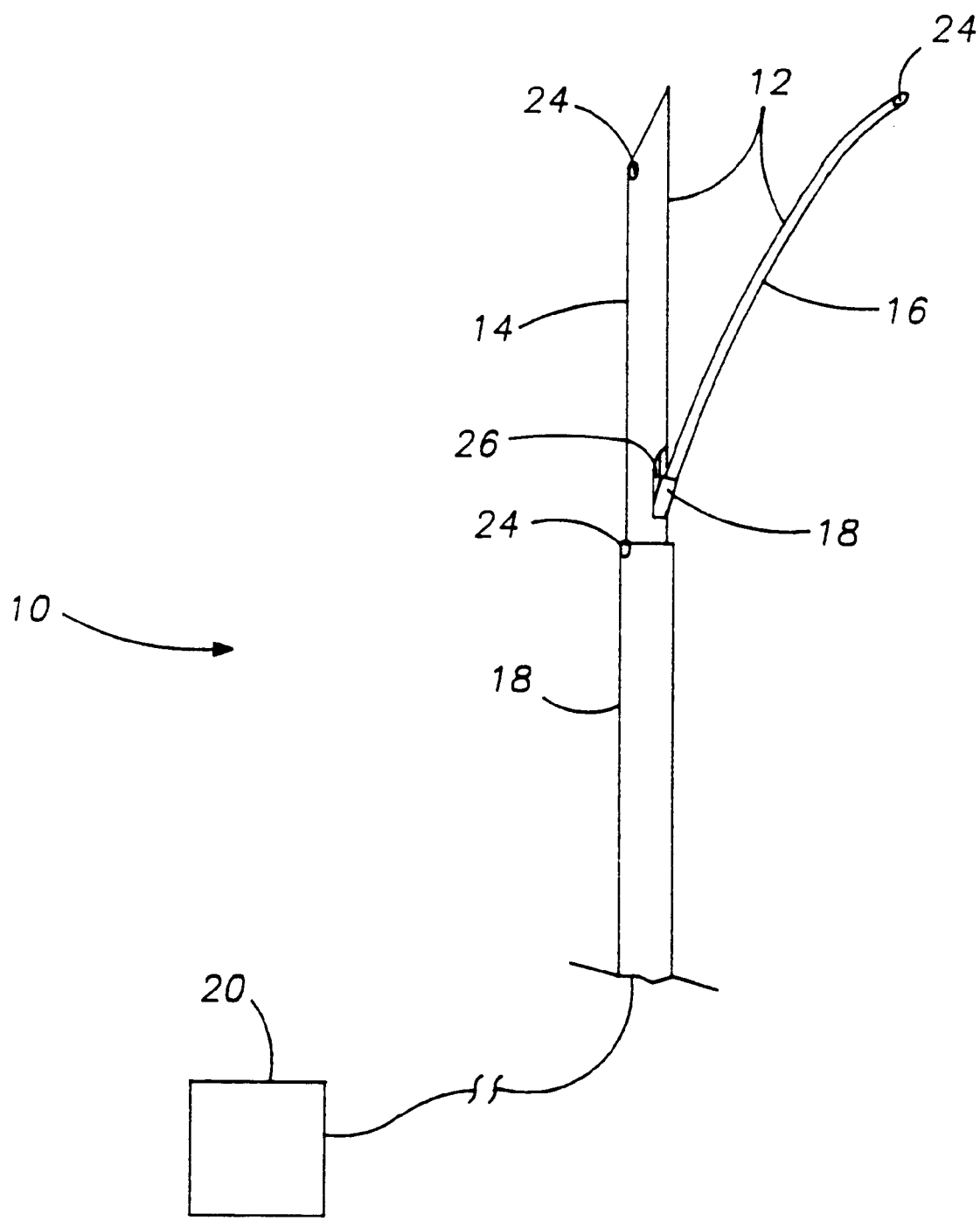
FIG. 1 is a perspective view of the multiple antenna ablation apparatus of the present invention illustrating a primary antenna and a single laterally deployed secondary antenna.

As shown in FIG. 1, an ablation treatment apparatus 10 includes a multiple antenna device 12 of adjustable length. Multiple antenna device 12 includes a primary antenna 14 with an adjustable energy transfer surface or length, and one or more secondary antennas 16 that are typically introduced from a lumen formed at least partially in primary antenna 14. Secondary antennas are introduced in the primary antenna 14 after primary antenna 14 is positioned at a selected tissue site. Each secondary antenna 16 also has an adjustable energy transfer surface or length. The adjustability of the lengths permits ablation of a wide variety of geometric configurations of a targeted mass. Lengths of primary and secondary antennas 14 and 16 are adjusted, and primary antenna 14 is moved up and down, rotationally about its longitudinal axis, and back and forth, in order to define, along with sensors, the periphery or boundary of the ablated mass and ablate a variety of different geometries that are not always symmetrical.

Primary antenna 14 is constructed so that it can be introduced percutaneously or laparoscopicly into a solid mass. Primary antenna 14 can have a sharpened distal end 14' to assist introduction into the solid mass. Each secondary electrode 16 is constructed to be less structurally rigid than primary antenna 14. This is achieved by, (i) choosing different materials for antennas 14 and 16, (ii) using the same material but having less of it for secondary antenna 16, e.g., secondary antenna is not as thick as primary electrode 14, or including another material in one of the antennas 14 or 16 to vary their structural rigidity. For purposes of this disclosure, structural rigidity is defined as the amount of deflection that an antenna has relative to its longitudinal axis. It will be appreciated that a given antenna will have different levels of rigidity depending on its length. Primary and secondary antennas can be made of a variety of conductive materials, both metallic and non-metallic. One suitable material is type 304 stainless steel of hypodermic quality. The rigidity of primary antenna 14 is greater than secondary antenna 16. Depending on the application, the rigidity of secondary antenna 16 can be about 10%, 25%, 50%, 75% and 90% of the rigidity of primary antenna 14.

Primary and secondary antennas 12 and 14 can be made of a variety of conductive materials, both metallic and nonmetallic. In some applications, secondary electrode 16 can be made of a shaped memory metal, such as NiTi, commercially available from Raychem Corporation, Menlo Park, Calif.

Each of primary or secondary antenna 14 or 16 can have different lengths. Suitable lengths include but are not limited to 17.5 cm, 25.0 cm. and 30.0 cm. The actual length of an antenna depends on the location of the targeted solid mass to be ablated, its distance from the skin, its accessibility as well as whether or not the physician chooses a laparoscopic, percutaneous or other procedure. Further, ablation treatment apparatus 10, and more particularly multiple antenna device 12, can be introduced through a guide to the desired tissue mass site.

An insulation sleeve 18 is positioned around an exterior of one or both of the primary and secondary antennas 14 and 16 respectively. Preferably, each insulation sleeve 18 is adjustably positioned so that the length of antenna providing an ablation delivery surface can be varied. Each insulation sleeve 18 a primary antenna 14 can include one or more apertures. This permits the introduction of a secondary antenna 16 through primary antenna 14 and insulation sleeve 18.

In one embodiment insulation sleeve can comprise a polyamide material, with a sensor positioned on top of the polyamide insulation, and a 0.002 inch shrink wrap. The polyamide insulating layer is semi-rigid. The sensor can lay down substantially the entire length of the polyamide.

An energy source 20 is connected with multiple antenna device 12 with one or more cables 22. Energy source 20 can be an RF source, microwave source, short wave source, laser source and the like. Multiple antenna device 12 can be comprised of primary and secondary antennas 14 and 16 that are RF antennas, microwave antennas, as well as combinations thereof. Energy source 20 may be a combination RF/microwave box. Further a laser optical fiber, coupled to a laser source 20 can be introduced through one or both of primary or secondary antennas 14 and 16. One or more of the primary or secondary antennas 14 and 16 can be an arm for the purposes of introducing the optical fiber.

One or more sensors 24 are positioned on interior or exterior surfaces of primary antenna 14, secondary antenna 16 or insulation sleeve 18. Preferably sensors 24 are positioned at primary antenna distal end 14, secondary antenna distal end 16 and insulation sleeve distal end 18. Sensors 24 permit accurate measurement of temperature at a tissue site in order to determine, (i) the extent of ablation, (ii) the amount of ablation, (iii) whether or not further ablation is needed and (iv) the boundary or periphery of the ablated mass. Further, sensors 24 prevent non-targeted tissue from being destroyed or ablated.

Sensors 24 are of conventional design, including but not limited to thermistors, thermocouples, resistive wires, and the like. Suitable thermal sensors 24 include a T type thermocouple with copper constantene, J type, E type, K type, fiber optics, resistive wires, thermocouple IR detectors, and the like. It will be appreciated that sensors 24 need not be thermal sensors.

Sensors 24 measure temperature and/or impedance to permit monitoring and a desired level of ablation to be achieved without destroying too much tissue. This reduces damage to tissue surrounding the targeted mass to be ablated. By monitoring the temperature at various points within the interior of the selected mass, a determination of the tumor periphery can be made, as well as a determination of when ablation is complete. If at any time sensor 24 determines that a desired ablation temperature is exceeded, then an appropriate feedback signal is received at energy source 20 which then regulates the amount of energy delivered to primary and/or secondary antennas 14 and 16.

Thus the geometry of the ablated mass is selectable and controllable. Any number of different ablation geometries can be achieved. This is a result of having variable lengths for primary antenna 14 and secondary antenna 16 ablation surfaces as well as the inclusion of sensors 24.

Preferably, secondary antenna 16 is laterally deployed out of an aperture 26 formed in primary antenna 14. Aperture 26 is typically positioned along the longitudinal axis of primary antenna 14.

Initially, primary antenna 14 is introduced into or adjacent to a target solid mass. Secondary antenna 16 is then introduced out of aperture 26 into the solid mass. There is wide variation in the amount of deflection of secondary antenna 16. For example, secondary antenna 16 can be deflected a few degrees from the longitudinal axis of primary antenna 14, or secondary antenna can be deflected in any number of geometric configurations, including but not limited to a "7" hook. Further, secondary antenna 16 is capable of introduced from primary antenna 14 a few millimeters from primary antenna, or a much larger distance. Ablation by secondary antenna 16 can begin a few millimeters away from primary antenna 14, or secondary electrode 16 can be advanced a greater distance from primary antenna 14 and at that point the initial ablation by secondary antenna 16 begins.

Figure 2:
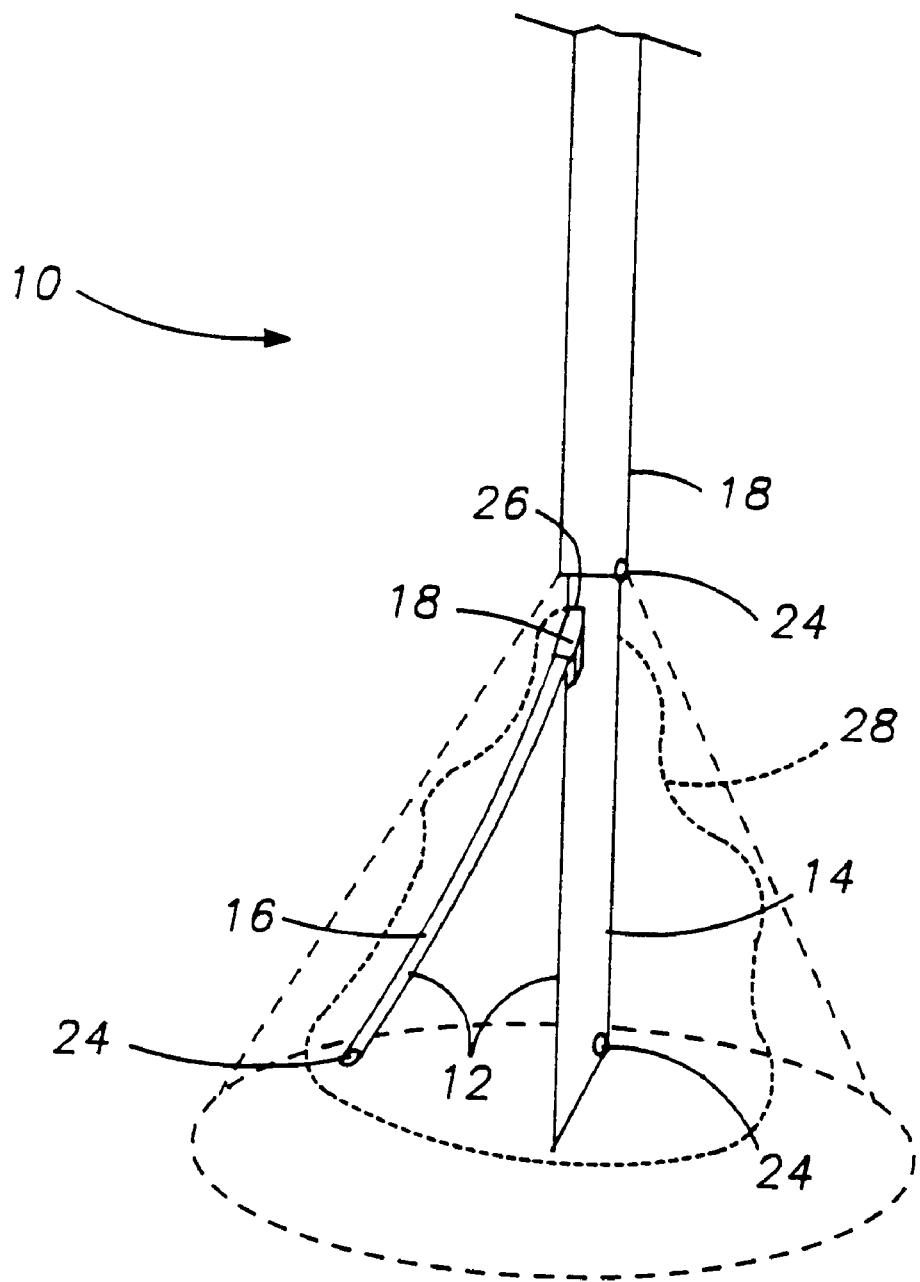
FIG. 2 is a perspective view of a conic geometric ablation achieved with the apparatus of FIG. 1.

Referring now to FIG. 2, primary antenna 14 has been introduced into a tumor 28, or other solid mass. Alter primary antenna 14 has been introduced secondary antenna 16 is advanced out of aperture 26 and into tumor 28. Insulation sleeves 18 are adjusted for primary and secondary antennas 14 and 16 respectively. RF, microwave, short wave and the like energy is delivery to antenna 16 in a monopolar mode (RF), or alternatively, multiple antenna device 12 can be operated in a bipolar mode (RF). Multi antenna device 12 can be switched between monopolar and bipolar operation and has multiplexing capability between antennas 14 and 16. In the monopolar mode ablation occurs between secondary antenna 16 and primary antenna 14. Secondary antenna 16 is retracted back into primary antenna 14, and primary antenna is then rotated. Secondary antenna 16 is then introduced in tumor 28. Secondary antenna may be introduced a short distance into tumor 28 to ablate a small area. It can then be advanced further into tumor 28 any number of times to create more ablation zones. Again, secondary antenna 16 is retracted back into primary antenna 14, and primary antenna 14 can be, (i) rotated again, (ii) moved along a longitudinal axis of tumor 28 to begin another series of ablations with secondary antenna 16 being introduced and retracted in and out of primary antenna 14, or (iii) removed from tumor 28. A number of parameters permit ablation of tumors, masses of different sign and shapes including a series of ablations having primary and secondary antennas 14 and 16 with variable length ablation surfaces and the use of sensor 24.

Figure 3:
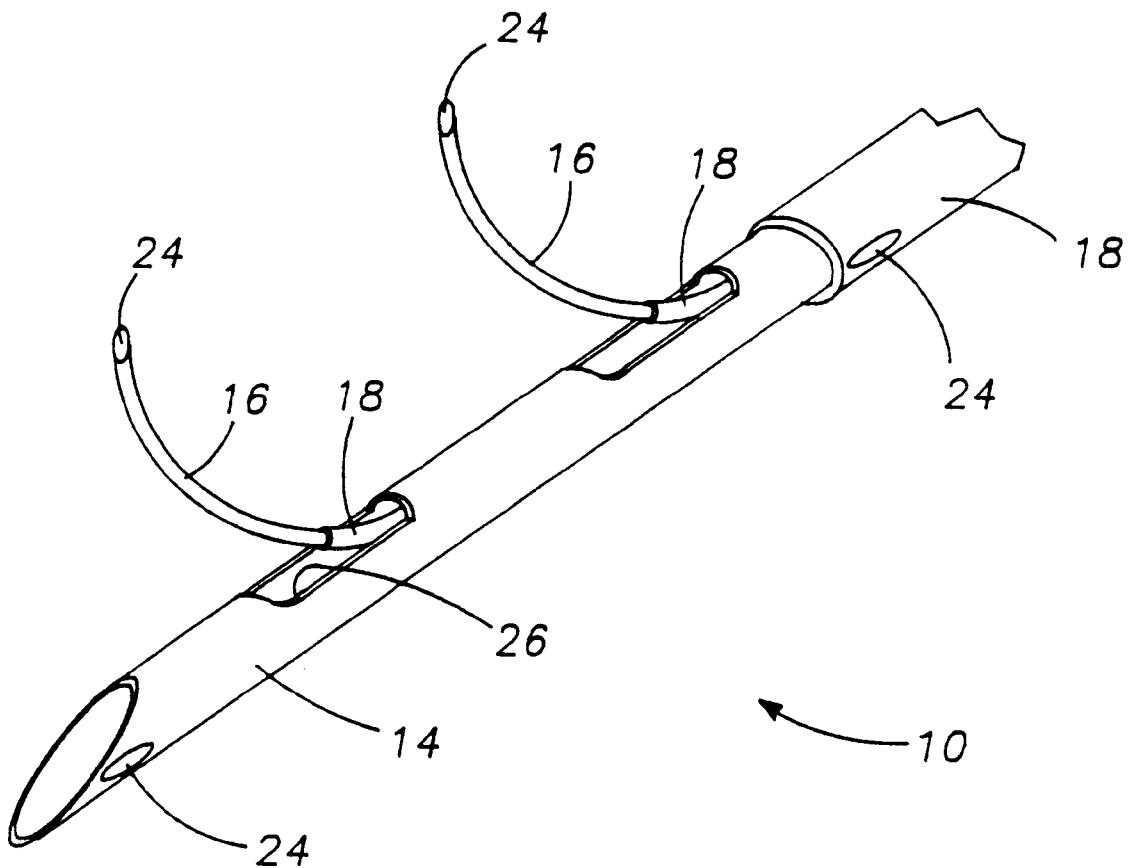
FIG. 3 is a perspective view of the multiple antenna ablation apparatus of the present invention with two secondary antennas.

As illustrated in FIG. 3, ablation treatment device can include two or more secondary antennas 16 which can be independently or dependently laterally deployed along different positions along the longitudinal axis of primary antenna 14. Each secondary antenna 16 is advanced out of a separate aperture 26 formed in the body of primary antenna 14. Multiple secondary antennas 16 can all be introduced along the same planes, a plurality of planes or a combination of both.

Figure 4:
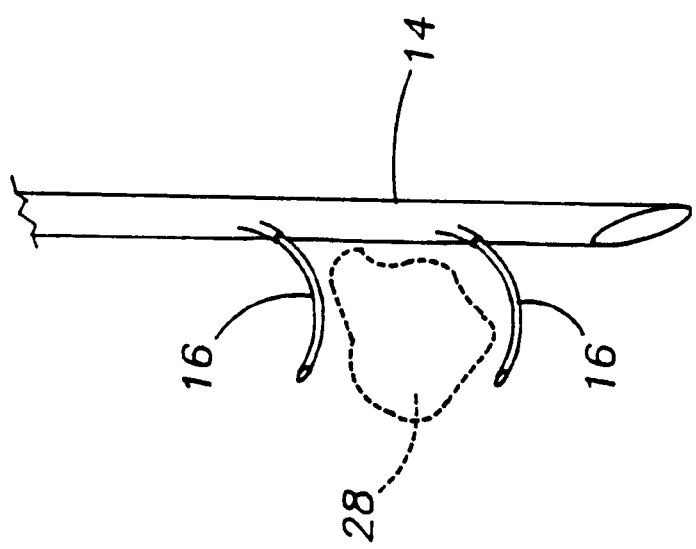
FIG. 4 is a perspective view illustrating the adjacent positioning next to a tumor of the apparatus of FIG. 3.

Primary antenna 14 can be introduced in an adjacent relationship to tumor 28, as illustrated in FIG. 4. As shown, two secondary antennas 16 are deployed from primary antenna 14 at opposite ends of irregularly shaped tumor 28. Operating in the bipolar mode, an ablation area is defined between the two secondary antennas 16. This particular deployment is particularly useful for small tumors, or where piercing tumor 28 is not desirable. Primary antenna 14 can be rotated, with secondary antennas 16 retracted into a central lumen of primary antenna 14, and another ablation volume defined between the two secondary antennas 16 is created. Further, primary electrode 14 can be withdrawn from its initial adjacent position to tumor 28, repositioned to another position adjacent to tumor 28, and secondary antennas 16 deployed to begin another ablation cycle. Any variety of different positioning may be utilized to create a desired ablation geometry for tumors of different geometries and sizes.

Figure 5:
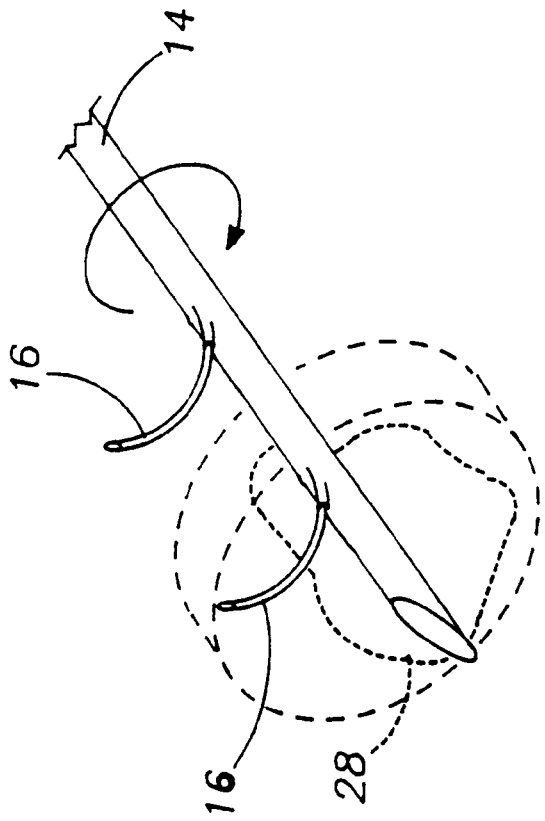
FIG. 5 is a perspective view illustrating the positioning of the apparatus of FIG. 3 in the center of a tumor, and the creation of a cylindrical ablation.

In FIG. 5, a center of tumor 28 is pierced by primary antenna 14, secondary antennas 16 are laterally deployed and retracted, primary antenna 14 is rotated, secondary antennas 16 are deployed and retracted, and so on until a cylindrical ablation volume is achieved. Multiple antenna device 12 can be operated in the bipolar mode between the two secondary antennas 16, or between a secondary antenna 16 and primary antenna 14. Alternatively, multiple antenna device 12 can be operated in a monopolar mode.

Figure 6C:
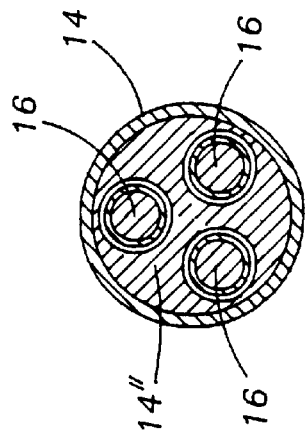
FIG 6(c) is a cross-sectional view of the apparatus of FIG. 6(b) taken along the lines 6(c)—6(c).
Figure 6B:
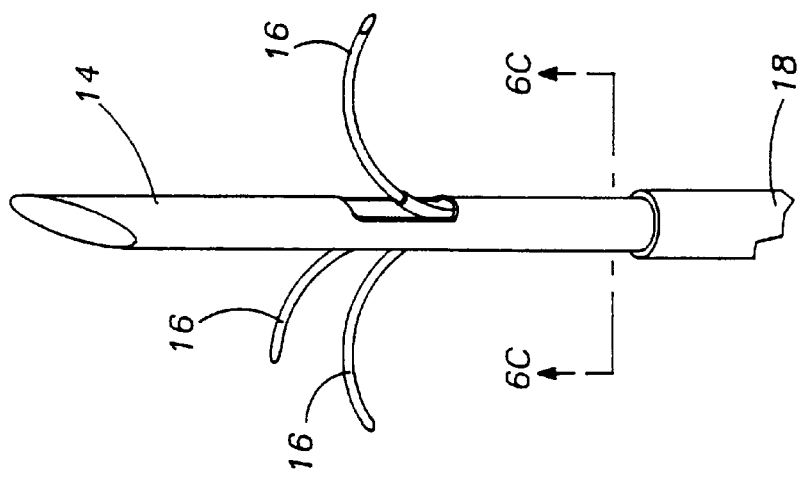
FIG. 6(b) is a perspective view of the multiple antenna ablation of the present invention illustrating three secondary antennas which provide a retaining and gripping function.
Figure 6A:
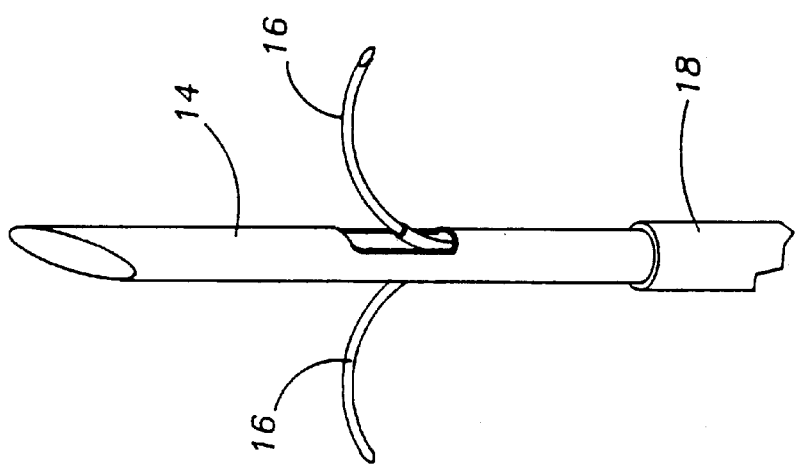
FIG. 6(a) is a perspective view of the multiple antenna ablation of the present invention illustrating two secondary antennas which provide a retaining and gripping function.
Figure 8:
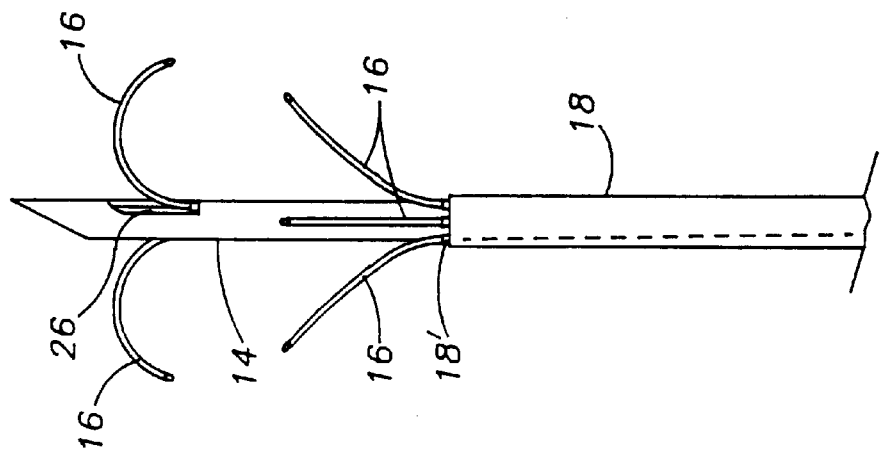
FIG. 8 is a perspective view of the multiple antenna ablation of the present invention illustrating the deployment of two secondary antennas from the primary antenna, and the deployment of three secondary antennas from the distal end of the insulation sleeve surrounding the primary antenna.
Figure 7:
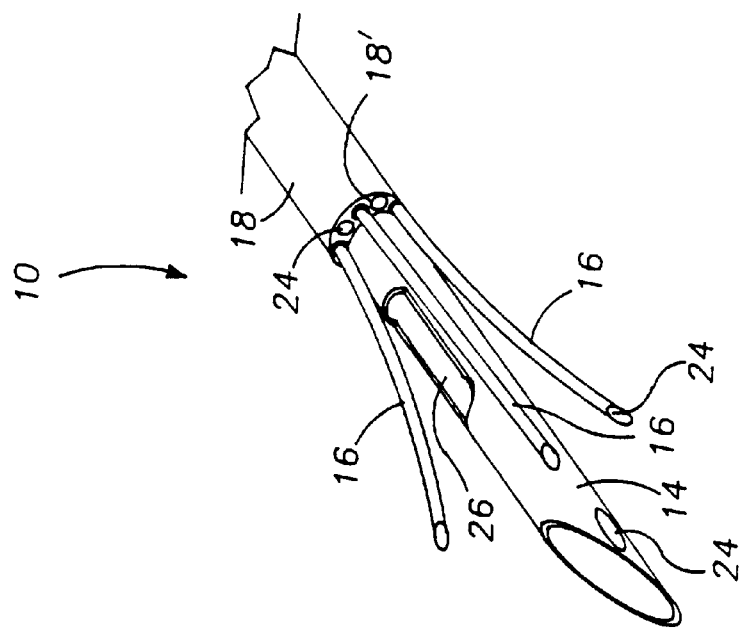
FIG. 7 is a perspective view of the multiple antenna ablation of the present invention illustrating the deployment of three secondary antennas from a distal end of the insulation sleeve surrounding the primary antenna.

Secondary antennas 16 can serve the additional function of anchoring multiple antenna device 12 in a selected mass, as illustrated in FIGS. 6(a) and 6(b). In FIG. 6(a) one or both secondary antennas 16 are used to anchor and position primary antenna 14. Further, one or both secondary antennas 16 are also used to ablate tissue. In FIG. 6(b), three secondary antennas are deployed and anchor primary antenna 14. FIG. 6(c) illustrates the infusion capability of multiple antenna device 12. Three secondary antennas 16 are positioned in a central lumen 14" of primary antenna 14. One or more of the secondary antennas 16 can also include a central lumen coupled to an infusion source. Central lumen 14" is coupled to an infusion source and delivers a variety of infusion mediums to selected places both within and outside of the targeted ablation mass. Suitable infusion mediums include but are not limited to, therapeutic agents, conductivity enhancement mediums, contrast agents or dyes, and the like. An example of a therapeutic agent is a chemotherapeutic agent. As shown in FIG. 7 insulation sleeve 18 can include one or more lumens for receiving secondary antennas 16 which are deployed out of an insulation sleeve distal end 18. FIG. 8 illustrates three secondary antennas 16 being introduced out of insulation sleeve distal end 18, and two secondary antennas 16 introduced through apertures 26 formed in primary antenna 14. As illustrated, the secondary electrodes introduced through apertures 26 provide an anchoring function. It will be appreciated that FIG. 8 shows that secondary antennas 16 can have a variety of different geometric configurations in multiple antenna device 12.

Resources, which can hardware, software, or a combination of both, are connected with sensors 24, primary and secondary antennas 14 and 16 and energy source 20 to provide an output for delivering and maintaining a selected energy at primary and secondary antennas 14 and 16, e.g., feedback control. Further, the resources provides an output that maintains a selected energy at primary and secondary antennas for a selected length of time.

Figure 9:
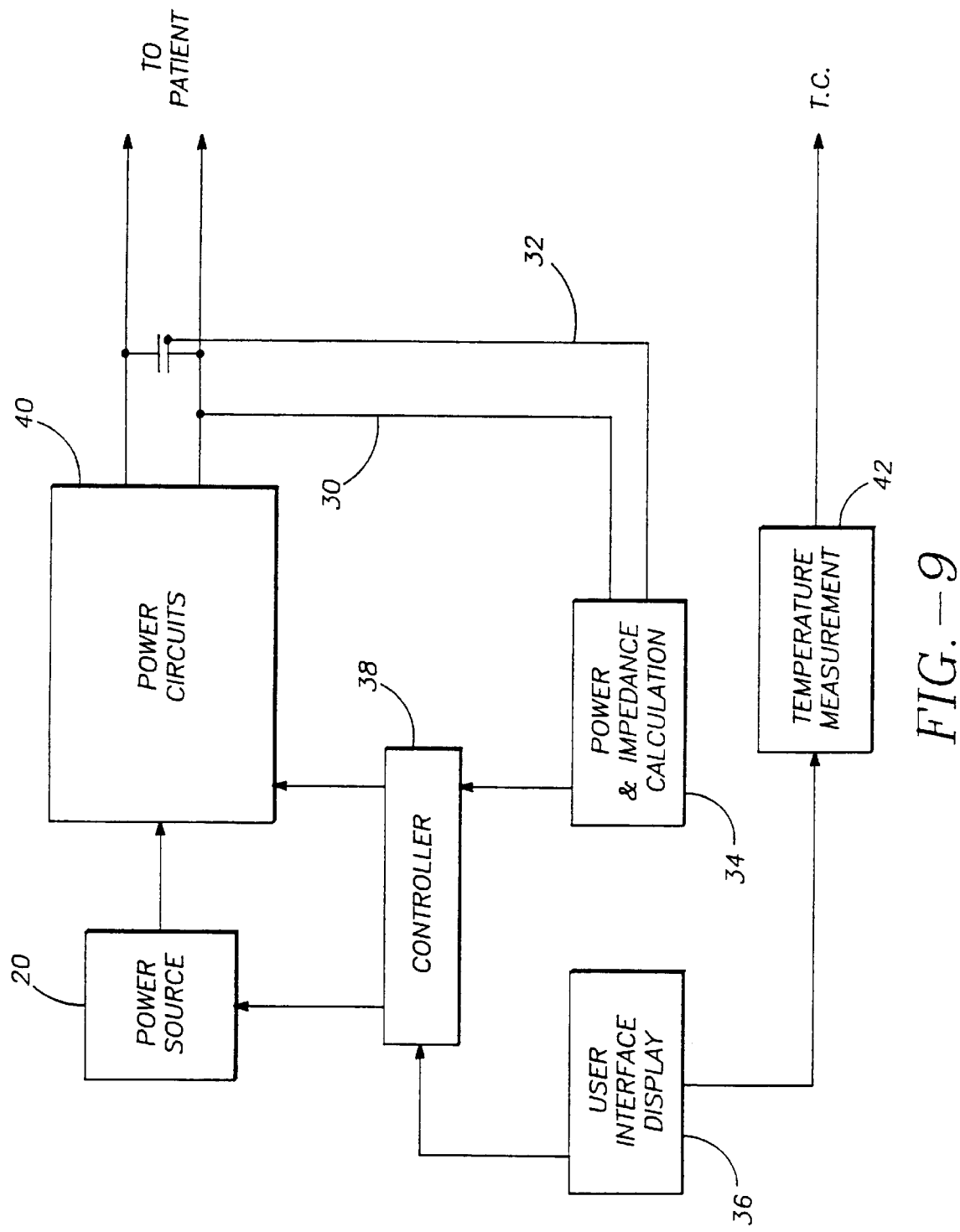
FIG. 9 is a block diagram illustrating the inclusion of a controller, energy source and other electronic components of the present invention.
Figure 10:
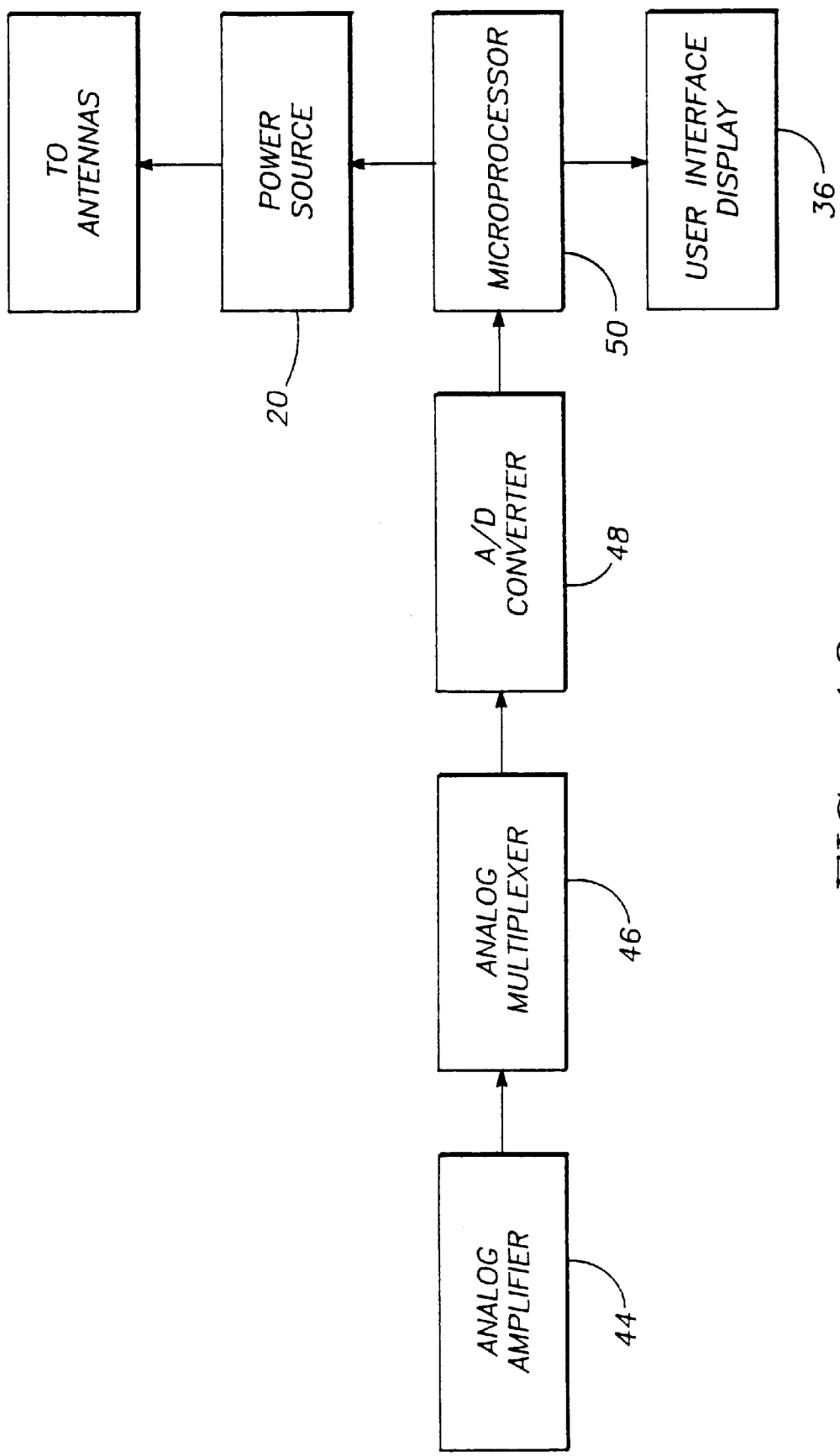
FIG. 10 is a block diagram illustrating an analog amplifier, analog multiplexer and microprocessor used with the present invention.

The following discussion pertains particularly to the use of an RF energy source and RF multiple antenna device 12. It will be appreciated that devices similar to those associated with RF multiple antenna device 12 can be utilized with laser optical fibers, microwave devices and the like. Referring now to FIG. 9 current delivered through primary and secondary antennas 14 and 16 is measured by current sensor 30. Voltage is measured by voltage sensor 32. Impedance and power are then calculated at power and impedance calculation device 34. These values can then be displayed at user interface and display 36. Signals representative of power and impedance values are received by controller 38.

A control signal is generated by controller 38 that is proportional to the difference between an actual measured value, and a desired value. The control signal is used by power circuits 40 to adjust the power output in an appropriate amount in order to maintain the desired power delivered at the respective primary and/or secondary antennas 14 and 16.

In a similar manner, temperatures detected at sensors 24 provide feedback for maintaining a selected power. The actual temperatures are measured at temperature measurement device 42, and the temperatures are displayed at user interface and display 36. A control signal is generated by controller 38 that is proportional to the difference between an actual measured temperature, and a desired temperature. The control signal is used by power circuits 40 to adjust the power output in an appropriate amount in order to maintain the desired temperature delivered at the respective sensor 24. A multiplexer can be included to measure current, voltage and temperature, at the numerous sensors 24, and energy is delivered between primary antenna 14 and secondary antennas 16.

Controller 38 can be a digital or analog controller, or a computer with software. When controller 38 is a computer it can include a CPU coupled through a system bus. On this system can be a keyboard, a disk drive, or other non-volatile memory systems, a display, and other peripherals, as are known in the art. Also coupled to the bus are a program memory and a data memory. User interface and display 36 includes operator controls and a display. Controller 38 can be coupled to imaging systems, including but not limited to ultrasound, CT scanners, X-ray, MRI, mammographic X-ray and the like. Further, direct visualization and tactile imaging can be utilized.

The output of current sensor 30 and voltage sensor 32 is used by controller 38 to maintain a selected power level at primary and secondary antennas 14 and 16. The amount of RF energy delivered controls the amount of power. A profile of power delivered can be incorporated in controller 38, and a preset amount of energy to be delivered can also be profiled.

Circuitry, software and feedback to controller 38 result in process control, and the maintenance of the selected power that is independent of changes in voltage or current, and are used to change, (i) the selected power, including RF, microwave, laser and the like, (ii) the duty cycle (on-off and wattage), (iii) bipolar or monopolar energy delivery and (iv) infusion medium delivery, including flow rate and pressure. These process variables are controlled and varied, while maintaining the desired delivery of power independent of changes in voltage or current, based on temperatures monitored at sensors 24.

Referring now to FIG. 9, current sensor 30 and voltage sensor 32 are connected to the input of an analog amplifier 44. Analog amplifier 44 can be a conventional differential amplifier circuit for use with sensors 24. The output of analog amplifier 44 is sequentially connected by an analog multiplexer 46 to the input of A/D converter 48. The output of analog amplifier 44 is a voltage which represents the respective sensed temperatures. Digitized amplifier output voltages are supplied by A/D converter 48 to a microprocessor 50.

Microprocessor 50 may be Model No. 68HC11 available from Motorola. However, it will be appreciated that any suitable microprocessor or general purpose digital or analog computer can be used to calculate impedance or temperature.

Microprocessor 50 sequentially receives and stores digital representations of impedance and temperature. Each digital value received by microprocessor 50 corresponds to different temperatures and impedances.

Calculated power and impedance values can be indicated on user interface and display 36. Alternatively, or in addition to the numerical indication of power or impedance, calculated impedance and power values can be compared by microprocessor 50 with power and impedance limits. When the values exceed predetermined power or impedance values, a warning can be given on user interface and display 36, and additionally, the delivery of RF energy can be reduced, modified or interrupted. A control signal from microprocessor 50 can modify the power level supplied by power source 36.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An ablation treatment apparatus, comprising:
a multiple antenna device including a primary antenna with a longitudinal axis, and a secondary antenna positionable in a lumen of the primary antenna and deployable at least partially in a lateral direction relative to the longitudinal axis with at least one radius of curvature, wherein a distal end of the primary antenna is sufficiently sharp to pierce tissue, and the primary and secondary antennas are configured to provide a selectable geometric ablation of a selected tissue mass;
an insulation sleeve positioned on an exterior of the primary antenna; and
one or more cables coupled to the multiple antenna device.

2. The apparatus of claim 1, wherein the primary and secondary antennas are RF antennas.

3. The apparatus of claim 1, wherein the primary and secondary antennas are microwave antennas.

4. The apparatus of claim 1, wherein the multiple antenna device includes at least two secondary antennas which are each independently laterally deployed along a different point along the longitudinal axis.

5. The apparatus of claim 1, wherein the multiple antenna device includes a number of secondary antennas that are all at least partially retractable into the primary antenna following an ablation and permit repositioning of the primary antenna.

6. The apparatus of claim 5, wherein the primary antenna is capable of rotational movement about its longitudinal axis following retraction of the secondary antennas into the primary antenna following an ablation.

7. The apparatus of claim 2, wherein the apparatus is configured to be switched between bipolar and monopolar operation.

8. The apparatus of claim 1, wherein the apparatus includes two secondary antennas positioned in the same plane.

9. The apparatus of claim 1, wherein the apparatus includes two secondary antennas that are deployed from the primary antenna in two different planes.

10. The apparatus of claim 2, wherein the apparatus is configured to operate in a monopolar mode.

11. The apparatus of claim 2, wherein the apparatus is configured to operate in a bipolar mode.

12. The apparatus of claim 1, wherein at least one of the primary or secondary antennas is hollow and adapted to receive an infusion medium from an infusion source to introduce the infusion medium into a selected tissue mass.

13. The apparatus of claim 12, wherein the infusion medium is a therapeutic agent.

14. The apparatus of claim 12, wherein the infusion medium is a conductivity enhancement medium.

15. The apparatus of claim 12, wherein the infusion medium includes a chemotherapeutic agent.

16. The apparatus of claim 1, further comprising:
    an energy source;
    one or more sensors coupled to the energy source and positioned at one of an interior or an exterior of the primary or secondary antennas to detect one of impedance or temperature; and
    a sensor feedback apparatus coupled to the sensors for maintaining a tissue adjacent to one of the primary or secondary antennas at a desired temperature.

17. The apparatus of claim 1, further comprising:
    one or more sensors positioned at one of an interior or an exterior of the primary or secondary antennas to detect one of impedance or temperature; and
    resources connected with the sensors, the antennas and an energy source, the resources providing an output for delivering and maintaining a selected energy at the antennas.

18. The apparatus of claim 17, wherein the resources provide an output that maintains a selected energy at the antennas for a selected length of time.

19. The apparatus of claim 17, wherein each of the primary and secondary antennas is independently connected to the resources, and the resources generate an independent output for each antenna.

20. The apparatus of claim 1, wherein the primary antenna is hollow and includes at least one aperture formed along the longitudinal axis of the primary antenna to laterally deploy at least one secondary antenna.

21. The apparatus of claim 1, wherein the primary antenna is hollow and includes first and second apertures formed along the longitudinal axis of the primary antenna to laterally deploy a first and a second secondary antenna out of the first and second apertures.

22. The apparatus of claim 1, further comprising:
    a temperature sensor coupled to one of the primary antenna or the secondary antenna.

23. The apparatus of claim 1, wherein the secondary antenna is configured to measure impedance.

24. The apparatus of claim 1, further comprising:
    an impedance measurement device advanceable from the primary antenna.

25. The apparatus of claim 1, wherein the insulation sleeve is in a surrounding relationship to the primary antenna, and a distal end of the insulation sleeve includes an aperture for introducing the secondary antenna.

* * * * *